(12) United States Patent
Shih

(10) Patent No.: US 8,426,466 B2
(45) Date of Patent: Apr. 23, 2013

(54) COMPOSITIONS AND METHODS FOR ENHANCING ACTIVE AGENT ABSORPTION

(75) Inventor: Chung Shih, Sandy, UT (US)

(73) Assignee: Nexus Pharma, Inc., Salt Lake City, UT (US)

( * ) Notice: Subject to any disclaimer, the term of this patent is extended or adjusted under 35 U.S.C. 154(b) by 1075 days.

(21) Appl. No.: 11/805,202

(22) Filed: May 21, 2007

(65) Prior Publication Data

US 2007/0269500 A1 Nov. 22, 2007

Related U.S. Application Data

(60) Provisional application No. 60/747,900, filed on May 22, 2007.

(51) Int. Cl.
*A61K 31/235* (2006.01)

(52) U.S. Cl.
USPC .......................................... 514/532; 424/400

(58) Field of Classification Search .................. None
See application file for complete search history.

(56) References Cited

U.S. PATENT DOCUMENTS

| | | | |
|---|---|---|---|
| 4,406,896 A | 9/1983 | Higuchi et al. | |
| 5,651,985 A * | 7/1997 | Penners et al. | 424/469 |
| 5,773,647 A | 6/1998 | Leone-Bay et al. | |
| 5,817,624 A | 10/1998 | Yang et al. | |
| 2007/0269500 A1 | 11/2007 | Shih | |

FOREIGN PATENT DOCUMENTS

| | | |
|---|---|---|
| CN | 1857727 | 11/2006 |
| WO | WO 01/54514 | 8/2001 |
| WO | WO 01/92206 | 12/2001 |
| WO | WO 03/057170 | 7/2003 |

OTHER PUBLICATIONS

Naito et al. Yakugaku Zasshi, 78, 682-683, 1958.*
Caplus Entry for Naito et al. Yakugaku Zasshi, 78, 682-683, 1958, accession No. 1958:89288.*
Takagi et al. Annals of Surgery, 228(1), 106-111, 1998.*
Guggi et al. J Controlled Release 92, p. 125-135, 2003.*
Rozwarski et al. Science, 279, p. 98-102, 1998.*
Meng, B. et al., "Hypoglycemic effect of insulin W/O microemulsions following intestinal administration to rats." Zhongguo Yaoke Daxue Xuebao. 2006,37(4), 304-307, ISSN: 1000-5048. See abstract (absorption enhancer Na 8-(2-hydroxybenzamido)caprylate).
Andrea Leone-Bay et al, 4-[4-[(2-Hydroxybenzol) amino] phenyl]butyric Acid as a Novel Oral Delivery Agent for Recombinant Human Growth Hormone. J. Med. Chem. 1996, 39, 2571-2578.
Andrea Leone-Bay et al, Synthesis and Evaluation of Compounds That Facilitate the Gastrointestinal Absorption of Heparin. J. Med. Chem. 1998, 41, 1163-1171.

* cited by examiner

*Primary Examiner* — Nissa Westerberg
(74) *Attorney, Agent, or Firm* — Thorpe North & Western LLP

(57) ABSTRACT

Compositions and methods for enhancing the absorption of active agents across the mucosa of animal subjects are provided. Methods of administration and appropriate dosage forms are also provided.

20 Claims, No Drawings

COMPOSITIONS AND METHODS FOR ENHANCING ACTIVE AGENT ABSORPTION

The present application claims the benefit of U.S. Provisional Patent Application No. 60/747,900, filed on May 22, 2006, the entirety of which is incorporated herein by reference.

BACKGROUND OF THE INVENTION

The effectiveness of a drug regimen is often highly dependent on achieving the necessary bioavailability of the drug once it is administered. Poor bioavailability of a drug makes it necessary to administer higher doses in order to achieve efficacy, but higher dosage requirements can lead to toxicity, undesirable side effects, and/or decreased patient compliance. Although the gastrointestinal tract is a common route for drug delivery, not all drugs are well absorbed through the lining of the gastrointestinal tract. In the case of some drugs, their polar nature or hydrophilic character may make them difficult to be absorbed. For example, drugs of high molecular weight molecules are difficult to successfully administer orally, because the acidic conditions and high enzymatic activity in the stomach can degrade such drugs. Delivering drugs through other routes, such as buccal, sublingual, rectal, nasal, vaginal mucosa, is one way to provide systemic access for drugs while avoiding the hostile environment of the gastrointestinal tract. However, for this to be successful, the drug administered must overcome the resistance of these membranes to absorption. It is therefore clear that any factor that enhances the rate of absorption through such surfaces will result in improved clinical efficacy of many drug therapies.

Early efforts to enhance the absorption, and therefore bioavailability, of drugs include the use of adjuvants, such as surface active agents, including ionic and non-ionic surfactants to increase biomembrane permeability. However, use of some adjuvants is attended by the risk of damaging the biomembrane. Therefore, a need continues to exist for compositions that safely promote the absorption of poorly absorbed drugs.

SUMMARY OF THE INVENTION

A composition for enhancing transmucosal absorption of an active agent can comprise a) at least one active agent; and b) an absorption enhancer having the formula:

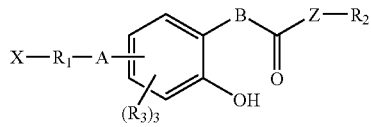

or a pharmaceutically acceptable salt thereof. In this formula, $R_1$ can be null, $C_1$-$C_{12}$ alkylene, $C_2$-$C_{12}$ alkenylene, arylene, or substituted alkylene, alkenylene, or arylene. The substituted alkylene, alkenylene, or arylene can be substituted with N, O, S, or P. Further, $R_2$ can be hydrogen, $C_1$-$C_{12}$ alkyl, $C_2$-$C_{12}$ alkenyl, aryl, or cycloalkyl; and each $R_3$ can independently be hydrogen, $C_1$-$C_{12}$ alkyl, $C_2$-$C_{12}$ alkenyl, or aryl, or substituted alkyl, alkenyl, or aryl, said substituted alkyl, alkenyl, or aryl being substituted with N, O, S, or P. X can be a tertiary amine, quaternary amine, tertiary sulfur, carboxylic acid, sulfide, sulfonic acid, sulfenic acid, sulfoxide, phosphoric acid, phosphonic acid, poly(ethylene glycol), saccharide, oligosaccharide, polyol, polyvinylpyrrolidone, polyvinyl alcohol, polyacrylic acid, chitosan, or a combination thereof. A can be null or a coupling moiety such as ether, amide, or ester; B can be null, —$CH_2$—, O, S, or NH; and Z can be null, O, S, NH, or NR where R is lower alkyl, or wherein Z is joined with $R_2$ to form a heterocyclic ring.

The composition of the present invention may be formulated into various dosage forms configured to bring the composition into effective contact with a mucosal surface of a subject, which includes external and internal mucosal surfaces of the body. Oral or administration can be used to contact the composition with the mucosal surfaces of the intestines, whereas a buccal administration can be used to transmucosally deliver the composition through the mucosal surfaces within the oral cavity. Exemplary dosage forms for delivery include tablets, capsules, powders, suspensions, creams, and suppositories.

The present invention is also drawn to methods of enhancing transmucosal absorption of active agents in a subject, which comprises administering a composition to the subject so that the composition comes into effective contact with a mucosal surface of the subject. The composition can be the same as that described above.

DETAILED DESCRIPTION OF THE PREFERRED EMBODIMENT(S)

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

It is to be noted that, as used in this specification and the appended claims, the singular forms "a," "an," and "the" include plural referents unless the context clearly dictates otherwise.

As used herein, "administration," and "administering" refer to the manner in which a drug, formulation, or composition is introduced into the body of a subject. Administration can be accomplished by various art-known routes such as oral, parenteral, transdermal, inhalation, implantation, etc. Thus, an oral administration can be achieved by swallowing, chewing, or sucking an oral dosage form comprising active agent(s). Parenteral administration can be achieved by injecting a composition intravenously, intra-arterially, intramuscularly, intrathecally, or subcutaneously, etc. Transdermal administration can be accomplished by applying, pasting, rolling, attaching, pouring, pressing, rubbing, etc., of a transdermal preparation onto a skin surface. Similarly, transmucosal administration can be accomplished by applying, pasting, rolling, attaching, pouring, pressing, rubbing, etc., of a transmucosal preparation onto a mucosal surface, as well as by spraying, irrigating the surface with the preparation. These and additional methods of administration are well known in the art.

The terms "effective amount," and "sufficient amount" may be used interchangeably and refer to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating a condition for which the active agent is known to be effective. Various biological factors may affect the ability of a substance to perform its intended task.

Therefore, an "effective amount" or a "therapeutically effective amount" may be dependent on such biological factors. Further, while the achievement of therapeutic effects may be measured by a physician or other qualified medical personnel using evaluations known in the art, it is recognized that individual variation and response to treatments may make the achievement of therapeutic effects a subjective decision. In some instances, a "therapeutically effective amount" of an active agent can achieve a therapeutic effect that is measurable by the subject receiving the active agent. The determination of an effective amount is well within the ordinary skill in the art of pharmaceutical, medicinal, and health sciences.

The term "effective contact" as used herein refer to contact of a nature and duration sufficient to allow a desired effect to be achieved, e.g. effective contact of a preparation with a surface into which it is to be absorbed will allow a measurable amount, preferably also an effective amount, of an agent in the preparation to enter the tissues or bloodstream of a subject, depending on the application target.

As used herein, "carrier" or "inert carrier" refers to typical compounds or compositions used to carry active ingredients, such as polymeric carriers, liquid carriers, or other carrier vehicles with which a bioactive agent, such as insulin, may be combined to achieve a specific dosage form. As a general principle, carriers do not substantially react with the bioactive agent in a manner which substantially degrades or otherwise adversely affects the active agent or its therapeutic potential.

When referring to alkyl, alkylene, alkenyl, alkenylene, or the like, it is understood that these terms include either linear or branched hydrocarbon chains. These hydrocarbon chains can optionally be substituted with N, O, S, or P, for example.

The term "null" is used herein to describe variables that, though included in a compound formulation, can be removed from the formulation. For example, if a variable "B" is said to be null, $—CH_2—$, O, S, or NH, the variable "B" can be removed from the formulation, or can be substituted with $—CH_2—$, O, S, or NH.

According to a more general embodiment of the present invention, a composition for achieving enhanced absorption of a drug or other active agent can comprise an effective amount of the active agent itself and an absorption enhancer or a pharmaceutically acceptable salt thereof. In one embodiment, the absorption enhancer may have the general formula:

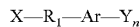
[Formula I]

where Ar can be an aromatic structure such as benzene or naphthalene; $Y_n$ can be OH, H, alkyl, aryl, alkenyl, alkynyl, cycloalkyl, carbamidoyl, ester, halogen, halogen-substituted alkyl, amino, alkoxyl, carbamyl, azo, thio, thioalkyl, cyano, sulfone, or alkyl sulfoxide groups, where n=2-5 of these groups or a combination thereof, and at least one of which is an OH; $R_1$ can be null, a saturated or unsaturated linear, branched or cyclic alkylene, or arylene, and optionally may be substituted with functional groups containing hetero-atoms such as N, O, S, or P ($R_1$ can be coupled to Ar through a coupling moiety); and X can include at least one hydrophilic moiety such as an ionizable functionality, e.g. tertiary amine, quaternary amine, tertiary sulfur, carboxylic acid, sulfide, sulfonic acid, sulfenic acid, sulfoxide, phosphoric acid, phosphonic acid, or a combination thereof, or other hydrophilic functionality such as poly(ethylene glycol), saccharides, polyvinyl alcohol, polyacrylic acid, chitosan and derivatives, or a combination of these functionalities.

While not wishing to be bound to a particular theory, it is thought that the improvement in absorption that an enhancer provides may be increased if the enhancer has an appropriate balance of lipophilic and hydrophilic properties. As can be seen from Formula I, absorption enhancers in accordance with the present invention can comprise a functional fragment of a small molecule adjuvant, a lipophilic component, and a hydrophilic component.

In a more specific embodiment, the absorption enhancer can be a derivative of salicylic acid. In one particular embodiment, such an enhancer can have the following formula:

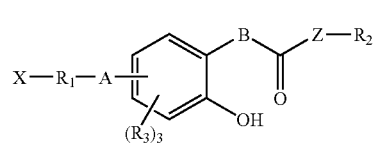
[Formula II]

where $R_1$ can be null, linear, or branched $C_1$-$C_{12}$ alkylene, $C_2$-$C_{12}$ alkenylene, arylene, or substituted alkylene, alkenylene, or arylene, said substituted alkylene, alkenylene, or arylene being substituted with N, O, S, or P; $R_2$ can be hydrogen or an aliphatic chain such as $C_1$-$C_{12}$ alkyl, $C_2$-$C_{12}$ alkenyl, or an aryl or cycloalkyl functional group; each $R_3$ can independently be hydrogen, $C_1$-$C_{12}$ alkyl, $C_2$-$C_{12}$ alkenyl, or aryl, or substituted alkyl, alkenyl, or aryl, said substituted alkyl, alkenyl, or aryl being substituted with N, O, S, or P; X can be tertiary amine, quaternary amine, tertiary sulfur, carboxylic acid, sulfide, sulfonic acid, sulfenic acid, sulfoxide, phosphoric acid, phosphonic acid, poly(ethylene glycol), saccharide, oligosaccharide, polyol, polyvinylpyrrolidone, polyvinyl alcohol, polyacrylic acid, chitosan, or a combination thereof. A can be null or a coupling moiety such as amide, ester, or ether; B can be null, $—CH_2—$, O, S, or NH; and Z can be null, O, S, NH, or NR where R is lower alkyl, or wherein Z is joined with $R_2$ to form a heterocyclic ring. It is noted that the aromatic ring can also be naphthalene or another fused aromatic ring structure.

When both B and Z are null, the absorption enhancer may have the formula:

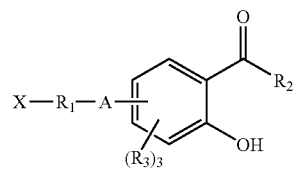
[Formula III]

where $R_1$, $R_2$, $R_3$, A, and X represent the same groups as with Formula II. In yet another alternative embodiment, when B is null, the absorption enhancer has the formula:

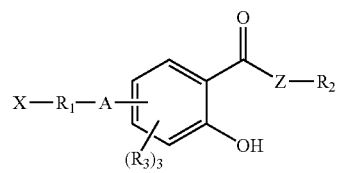
[Formula IV]

where $R_1$, $R_2$, $R_3$, Z, A, and X represent the same groups as with Formula II.

In a preferred aspect of any of the embodiments represented in Formulas I-IV, $R_1$ includes an amide, ether, or an ester group by which it is attached to the aromatic ring. In another preferred aspect of these embodiments, X is COOH.

The absorptive characteristics of the enhancers can also be affected by the overall lipophilicity of the molecule contributed by $R_1$ and $R_2$ as well as substitution(s) on the aromatic ring. For example, where X—$R_1$ (plus an amide linker moiety or other linker moiety) in Formula II is a HOOCCH$_2$CH$_2$CONH (and Z=NH), a more optimal length of $R_2$ can provide the maximal enhancement in absorbability, while a shorter or longer chain length may provide a lesser benefit in some circumstances. In addition, absorbability may be affected by the position of the moiety containing $R_1$ and the amide group of the moiety containing $R_2$. In the same example, where the moiety containing $R_1$ is in a para orientation relative to the moiety containing $R_2$, achieving the maximal absorption enhancement may benefit from a shorter $R_2$ chain than when these two moieties are in a meta orientation relative to one another. Accordingly, a preferred length of an aliphatic chain in $R_2$ is 3 to 12 carbons, with a still more preferred length being 4 to 8 carbons when the moiety containing $R_1$ is para to moiety containing $R_2$. When the moiety containing $R_1$ and moiety containing $R_2$ are in meta position, the preferred $R_2$ chain length may be 5 to 10 carbons. In the case when X is a carboxylic acid (HOOC—) and Z—$R_2$ is NH$_2$, preferred size of the aliphatic chain length $R_1$ is 4 to 12 carbons when X—$R_1$ and Z—$R_2$ are in para position and 5 to 12 carbons when they are in meta position.

In the salicylate-based enhancers described in Formulas II-IV, the basic structure of salicylic acid is preserved to the extent that an OH group is always present at carbon 2 of the ring (and therefore is always ortho to the carbonyl carbon at position 1). Furthermore, the lipophilic functionality $R_2$ extends from the carbonyl, ester, or amide group at position 1, while $R_1$ is attached to the ring at any one of carbons 3-6. However, other structural arrangements that will provide both lipophilic and hydrophilic properties are considered within the scope of this invention. For example, $R_3$ may be attached, directly or through an ether, ester, or amide linkage, at any of carbons 3-6 instead of $R_1$, with an alkyl or alkenyl group providing lipophilicity and a hydrophilic group (such as carbonyl, nitro, cyano, tri-chloro- or tri-fluoro-substituted groups) providing hydrophilicity. Note, however, that in these arrangements, the relative orientation of the hydroxyl and carbonyl remains the same (i.e. ortho), as in Formulas II-IV. Also, as with those previously described embodiments, the length of the carbon chain in $R_2$ may be adjusted to attain the optimal degree of absorption.

Biologically and chemically active agents that can be made more useful by enhancing their absorption are exemplified, without limitation, by the following: growth hormones, including human growth hormones (hGH), bovine growth hormones, and porcine growth hormones; growth hormone releasing hormones; interferons; cytokines; naturally occurring or recombinant insulins, including porcine, bovine, and human, optionally having counter ions including sodium, zinc, calcium, and ammonium; insulin-like growth factors, including IGF-1; heparin, including unfractionated heparin, heparinoids, dermatans, chondroitins, low molecular weight heparin, very low molecular weight heparin, and ultra-low molecular weight heparin; calcitonin, including salmon, eel, and human; erythropoetin; granulocyte-colony stimulating factor; atrial naturetic factor; antigens; monoclonal antibodies; somatostatin; protease inhibitors; adrenocorticotropin; gonadotropin releasing hormone; oxytocin; leutinizing hormone releasing hormone; follicle stimulating hormone; glucocerebrosidase; thrombopoietin; human granulocyte colony stimulating factor; prostaglandins; cyclosporin; vasopressin; cromolyn sodium; vancomycin; desferrioxamine; parathyroid hormone, including its fragments; vitamins; polyethylene glycol derivatives of these compounds, or any combination of these, as well as other proteins, polypeptides, hormones, polysaccharides, carbohydrates, and other organic compounds exhibiting poor bioavailability when administered to a subject. Other agents include vaccines, nucleotides, and antiviral agents.

The compositions of the present invention are useful for administering biologically or chemically active agents to animals, including but not limited to birds such as chickens, and mammals such as cows, pigs, dogs, cats, primates, and particularly humans. The present invention may also be utilized to deliver agents such as pesticides and hormone disruptors to insects.

The compositions of the present invention can be particularly useful in enhancing the absorption of active agents across mucosal surfaces outside of the small and large intestines, so as to provide a viable alternate delivery route to a subject's system other than by oral routes. Besides avoiding the likely degradation an active agent would encounter in the gastrointestinal environment, transmucosal administration can be a less invasive alternative to oral administration, due to the relatively easy access to a number of mucosal surfaces, such as in the buccal cavity, nose, vagina, and rectum. Other possible transmucosal routes include the sublingual, ocular, intraduodenal, intracolonic, pulmonary mucosa, jejunum mucosa, and ileum mucosa. The compositions of the present invention also encompass both traditional oral delivery routes as well as through oral mucosa. As such, the present invention also provides methods of enhancing absorption of active agents in a subject by administering a composition comprising an active agent and an enhancer so that it comes into effective contact with a mucosal surface of the subject, such as any of the surfaces listed above. The dosage form utilized in such a method will depend on the mucosal surface involved, and the manner of access provided to the surface.

Accordingly, dosage forms for providing enhanced absorption of active agents by any of these routes can comprise the active agent(s) and any absorption enhancer in accordance with the present invention. For oral administration, dosage forms include liquid suspensions or elixirs, capsules, coated and uncoated tablets, quick dissolving formulations, lozenges, gels, pastes, etc. Buccal administration can include buccal patches, tablets, lozenges, gels, pastes, etc. Rectal and vaginal dosage forms include liquids, gels, pastes, creams, and suppositories. Nasal administration may be accomplished with liquids, gels, pastes, or dry powders.

As appropriate to the form utilized, these dosage forms may each also comprise excipients in addition to the active agent and enhancer. For example, liquid oral dosage forms may include diluents, solubilizers, flavorants, taste masking agents, surfactants, buffering agents, preservatives, antioxidants, colorants, ethanol, propylene glycol, saccharides, and polyethylene glycol, as well as other appropriate additives known to those skilled in the art, and any combination thereof. Solid oral dosage forms such as tablets, coated tablets, capsules, and powders may be prepared by conventional skills in the art, and include excipients such as fillers, diluents, disintegrants, lubricants, glidents, plasticizers, colorants, flavorants, taste masking agents, saccharides, surfactants, binders, buffering agents, preservatives, antioxidants, colorants, polymer coatings, pore formers, and any combination thereof. Formulations for nasal administration may require a propellant. Suppositories may also contain suppository bases to provide proper consistency, such as coconut butter, polyethylene glycol, etc. Any of these dosage forms may optionally include any of a number of enzyme inhibitors known in the art such as actinonin or epiactinonin, and derivatives thereof; aprotinin; and Bowman-Birk inhibitor.

EXAMPLES

Example 1

Synthesis of Methyl 4-aminosalicylate

4-Aminosalicylic acid (12.3 g) is placed in a round bottom flask. The flask is charged with 150 mL of methanol and 20 mL of concentrated sulfuric acid. The reaction mixture is brought to gentle reflux for 1 day, and then allowed to cool to room temperature. The mixture is further chilled in a freezer and methyl 4-aminosalicylate bisulfate is crystallized. The crystals are collected and washed with cold methanol to afford 15.8 g of the product as off-white needles.

Example 2

Synthesis of Methyl 4-(3-carboxy-propionylamino)-2-hydroxybenzoate

Methyl 4-aminosalicylate bisulfate (5 g) is placed in a 50-mL round bottom flask. The flask is charged with 20 mL of methylene chloride and 15 mL of triethylamine. Finally, succinic anhydride (2.75 g) is added. The reaction mixture is then allowed to stir at ambient conditions overnight. Solvents are removed under reduced pressure, yielding a viscous residue, to which 1 N HCl is added. Methyl (3-carboxy-propionylamino)-2-hydroxybenzoate is yielded as tan powder. The powders are collected by filtration, washed with water, and dried.

Example 3

Synthesis of N-n-hexyl 4-(3-carboxy-propionylamino)-2-hydroxybenzamide

Methyl 4-(3-carboxy-propionylamino)-2-hydroxybenzoate from Example 2 (1 g) is dissolved in 15 mL of methanol. n-Hexylamine (5 mL) is added to this solution, and the reaction mixture is brought to mild reflux for 2 days. Solvents are removed under vacuum and residue acidified using 1 N HCl. N-n-hexyl 4-(3-carboxy-propionylamino)-2-hydroxybenzamide precipitate is collected, washed with water, and dried.

Example 4

Synthesis of 4-(3-carboxy-propionylamino)-2-hydroxybenzamide

Methyl 4-(3-carboxy-propionylamino)-2-hydroxybenzoate (1 g) from Example 2 is dissolved in 5 mL of 28% ammonium hydroxide solution. The reaction mixture is stirred at ambient conditions for 16 hours. In an ice-water bath, the solution is carefully acidified using concentrated hydrochloric acid. The precipitate is collected by filtration, washed with water and dried.

Example 5

Synthesis of 4-aminosalicylamide

Methyl 4-aminosalicylate bisulfate (5 g) is suspended in 20 mL of methanol. To the solution, 20 mL of 28% ammonium hydroxide is added slowly until all solid is dissolved. The reaction mixture is stirred at ambient conditions overnight. Solvent is removed under reduced pressure and water is lyophilized. The residue is collected, washed with minimum amount of ice water and dried to yield 2.5 g of the product as off-white powders.

Example 6

Synthesis of 4-(9-carboxy-nonanoylamino)-2-hydroxybenzamide 4-aminosalicylamide (2 g) from Example 5 is charged with 20 mL of methylene chloride. To the solution, 3.3 g of methyl 10-chloro-10-oxodecanoate is added. The reaction is initiated by addition of 2.6 mL of triethylamine. The reaction mixture is allowed to stir at ambient conditions for 2 days. Solvent is removed and the residue is acidified using 1 N HCl. The precipitate is extracted into ethyl acetate. The organic layer is further extracted with 1 N NaOH and saturated NaCl solutions. After drying over anhydrous sodium sulfate, solvent is removed. The residue is reconstituted in tetrahydrofuran (10 mL) and 10 mL of 2 N NaOH is added. The solution is brought to gentle reflux for 2 hours. The disappearance of the methyl ester is followed by HPLC. When all ester is hydrolyzed, the solution is cooled and acidified and the product is extracted into ethyl acetate. The organic layer is washed with saturated NaCl and dried over anhydrous sodium sulfate. Solvent is removed under reduced pressure and the product is obtained as off-white powder.

Example 7

Synthesis of Methyl 2,5-dihydroxybenzoate 2,5-Dihydroxybenzoic acid (4 g) is dissolved in 20 mL of methanol. To the solution, 3 mL of concentrated sulfuric acid is added. The reaction mixture is brought to gentle reflux over 24 hours. Methanol is removed and the residue is diluted with water. The compound of interest is extracted into ethyl acetate. The organic layer is extracted with saturated sodium bicarbonate solution and dried over anhydrous sodium sulfate. Solvent is removed and the product is in the form of off-white powders.

Example 8

Synthesis of N-n-hexyl 2,5-dihydroxybenzamide

Methyl 2,5-dihydroxybenzoate (1 g) is dissolved in 10 mL of n-hexylamine. After overnight heating in an oil bath (60° C.), the mixture is cooled to room temperature. n-Hexylamine is removed under reduced pressure. The residue is dissolved in ethyl acetate and further extracted with 1 N HCl. The organic layer is extracted with saturated sodium bicarbonate and dried over anhydrous sodium sulfate. Solvent is removed under reduced pressure to yield the product as an off-white powder.

Example 9

Synthesis of N-n-hexyl 5-(3-carboxy-propionyloxy)-2-hydroxybenzamide

N-n-Hexyl 2,5-dihydroxybenzamide (1 g) is dissolved in 15 mL of methylene chloride. To the solution 0.75 g of succinic anhydride and 0.95 g of 4-N,N-dimethylaminopyridene is added. The reaction mixture is allowed to stir at ambient conditions over 24 hours. Solvent is removed and the residue is reconstituted in ethyl acetate and extracted twice with 1 N HCl to remove the catalyst. The organic layer is further extracted with saturated sodium chloride solution and dried over anhydrous sodium sulfate. Solvent is removed under reduced pressure to yield the product as an off-white powder.

Example 10

Synthesis of n-hexyl 2,4-dihydroxybenzoate 2,4-Dihydroxybenzoic acid (5 g) is added to 20 mL of n-hexanol. Concentrated sulfuric acid (5 mL) is added dropwise. The reaction mixture is heated at 60° C. for 6 days. Hexanol is removed under reduced pressure. The residue is recrystallized from methanol/water mixture. The crystals are collected, washed with cold methanol and dried.

Example 11

Synthesis of n-hexyl 4-(3-carboxy-propionyloxy)-2-hydroxybenzoate n-Hexyl 2,4-dihydroxybenzoate (2 g) is dissolved in 25 mL of methylene chloride. To the solution, 0.85 g of succinic anhydride and 1.05 g of 4-N,N-dimethylpyridene are added. The reaction mixture is allowed to stir at ambient conditions overnight. The reaction mixture is extracted with 1 N HCl, water and saturated sodium chloride solution. The organic layer is dried over anhydrous sodium sulfate. Solvent is removed under reduced pressure to yield the product as an off-white powder.

Example 12

Enhancement of Bioavailability of Insulin Using Absorption Enhancer

In a vial, 0.5 g of N-n-hexyl 4-(3-carboxy-propionylamino)-2-hydroxybenzamide from Example 3 is suspended in 2 mL of water. It is neutralized by 1 equivalent of sodium hydroxide. The pH is adjusted to 7-8 by 1N HCl and saturated sodium bicarbonate. Bovine pancreatic insulin (1.75 mL; Sigma, 10 mg/mL; in pH 8.2 HEPES buffer) is added and mixed by gentle swirling. The solution density is determined so that the required dose may be calculated.

The solution is then given to Sprague-Dawley rats (2-day fasting, female, 250-300 g, n=3), intracolonically. Blood samples are taken from the tail vein and glucose levels measured using an OneTouch® UltraSmart® blood glucose meter. The analysis yields a blood glucose profile in which increasing the dose of absorption enhancer results in greater decreases in blood glucose, as shown in Table 1.

TABLE 1

Blood glucose depression (in % of basal level) induced by intracolonically administrated bovine pancreatic insulin using N-n-hexyl 4-(3-carboxy-propionylamino)-2-hydroxybenzamide as the absorption enhancer

| Time | Dose of enhancer % Glucose Depression From Basal Level | | | | |
|---|---|---|---|---|---|
| (min) | 0 mg/kg | 5 mg/kg | 25 mg/kg | 100 mg/kg | 200 mg/kg |
| 0 | 100 | 100 | 100 | 100 | 100 |
| 30 | 94 ± 4 | 78 ± 9 | 52 ± 7 | 50 ± 8 | 46 ± 4 |
| 60 | 102 ± 7 | 83 ± 3 | 28 ± 3 | 29 ± 3 | 28 ± 3 |
| 90 | 105 ± 3 | 77 ± 5 | 29 ± 3 | 20 ± 2 | 33 ± 3 |
| 120 | 107 ± 7 | 99 ± 4 | 31 ± 8 | 19 ± 3 | 25 ± 3 |
| 150 | 94 ± 7 | 105 ± 6 | 29 ± 6 | 29 ± 6 | 26 ± 4 |
| 180 | 111 ± 7 | 96 ± 7 | 47 ± 8 | 22 ± 2 | 33 ± 2 |
| 210 | 113 ± 4 | 113 ± 8 | 67 ± 5 | 30 ± 6 | 29 ± 4 |
| 240 | 100 ± 7 | 105 ± 6 | 77 ± 5 | 49 ± 5 | 54 ± 7 |

Examples 13-22

The general procedure followed in Example 12 above is followed in Examples 13-22 (using different compounds and different dosages as set forth below), with the following results.

TABLE 2

Blood glucose depression from basal level as a function of absorption enhancer structure and dose

| Example No. | Formula | Enhancer X—R$_1$ (with amide coupling moiety) | Z—R$_2$ | Dose mg/Kg | Insulin mg/Kg | 50% depression at 60 min. |
|---|---|---|---|---|---|---|
| 13 | IV | 4-HOOC(CH$_2$)$_2$CONH | NH$_2$ | 200 | 7 | negative |
| 14 | IV | 4-HOOC(CH$_2$)$_2$CONH | NHC$_2$H$_5$ | 200 | 7 | negative |
| 15 | IV | 4-HOOC(CH$_2$)$_2$CONH | NHC$_4$H$_9$ | 100 | 7 | positive |
| 16 | IV | 4-HOOC(CH$_2$)$_2$CONH | NHC$_6$H$_{13}$ | 25 | 7 | positive |
| 17 | IV | 4-HOOC(CH$_2$)$_2$CONH | NHC$_8$H$_{17}$ | 25 | 7 | positive |
| 18 | IV | 4-HOOC(CH$_2$)$_2$CONH | NHC$_{10}$H$_{21}$ | 50 | 7 | positive |
| 19 | IV | 4-HOOCCH$_2$CH(CH$_3$)CH$_2$CONH | NHC$_6$H$_{13}$ | 200 | 7 | positive |
| 20 | IV | 4-HOOC(CH$_2$)$_2$CONH | OCH$_3$ | 200 | 7 | negative |
| 21 | IV | 4-HOOC(CH$_2$)$_2$CONH | OC$_2$H$_5$ | 200 | 7 | negative |
| 22 | IV | 4-HOOC(CH$_2$)$_2$CONH | OC$_4$H$_9$ | 50 | 7 | Positive |

It is noted that though Examples 13, 14, 20, and 21 are shown as "negative," that does not mean that no enhancement occurred. It only means that a 50% reduction in glucose levels was not reached in 60 minutes. As insulin reduces glucose levels in the blood, a depression in glucose levels indicates insulin reaching the blood efficaciously.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A composition, comprising:
    a) at least one active agent selected from the group consisting of a polypeptide, a hormone, a polysaccharide, prostaglandins, cyclosporin, cromolyn sodium, vancomycin, desferrioxamine and vitamins; and
    b) an absorption enhancer having the formula:

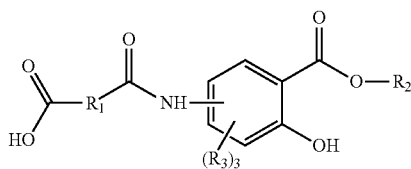

or a pharmaceutically acceptable salt thereof, wherein
   $R_1$ is null, $C_1$-$C_{12}$ alkylene, $C_2$-$C_{12}$ alkenylene, arylene, or substituted alkylene, alkenylene, or arylene, said substituted alkylene, alkenylene, or arylene being substituted with N, O, S, or P;
   $R_2$ is $C_4$-$C_{12}$ alkyl, $C_1$-$C_{12}$ alkyl, $C_2$-$C_{12}$ alkenyl, aryl, or cycloalkyl; and
   each $R_3$ is independently hydrogen, $C_1$-$C_{12}$ alkyl, $C_2$-$C_{12}$ alkenyl, or aryl, or substituted alkyl, alkenyl, or aryl, said substituted alkyl, alkenyl, or aryl being substituted with N, O, S, or P, wherein the composition is in a dosage form configured to bring a therapeutically effective amount of the at least one active agent into effective contact with a mucosal surface of a subject.

2. The composition of claim 1, wherein the moiety containing $R_1$ is para on the aromatic ring with respect to the moiety containing $R_2$.

3. The composition of claim 1, wherein the moiety containing $R_1$ is meta on the aromatic ring with respect to the moiety containing $R_2$.

4. The composition of claim 1, further comprising an enzyme inhibitor.

5. The composition of claim 1, formulated into a dosage form selected from the group consisting of tablet, capsule, lozenge, liquid solution, liquid suspension, paste, gel, cream, powder, patch, or suppository.

6. The composition of claim 5, wherein the dosage form is a liquid solution or suspension.

7. The composition of claim 5, wherein the dosage form is a patch.

8. The composition of claim 5, wherein the dosage form is a suppository.

9. The composition of claim 1, formulated in an oral dosage form.

10. The composition of claim 1, wherein the dosage form comprises an additive selected from the group consisting of diluents, solubilizers, excipients, flavorants, taste masking agents, surfactants, buffering agents, preservatives, antioxidants, colorants, fillers, disintegrants, lubricants, glidents, plasticizers, ethanol, pore formers, propylene glycol, saccharides, polyethylene glycol, and combinations thereof.

11. A method of enhancing transmucosal absorption of active agents in a subject, comprising administering a composition according to claim 1 to the subject so that the composition comes into effective contact with a mucosal surface of the subject.

12. The method of claim 11, wherein the mucosal surface is selected from the group consisting of buccal, sublingual, nasal, rectal, pulmonary, ocular, or vaginal.

13. The method of claim 11, wherein the composition is administered vaginally.

14. The method of claim 11, wherein the composition is administered rectally.

15. The method of claim 11, wherein the composition is administered nasally.

16. The method of claim 11, wherein the composition is administered orally.

17. The method of claim 16, wherein the active agent is absorbed through the duodenum, ileum, jejunum, or colon.

18. The method of claim 16, wherein the composition is administered in a dosage form selected from the group consisting of tablet, capsule, powder, elixir, and suspension.

19. The method of claim 18, wherein the dosage form is a liquid solution or suspension.

20. The method of claim 18, wherein the dosage form is a tablet or capsule.

* * * * *